US007833960B2

(12) United States Patent
Lei et al.

(10) Patent No.: US 7,833,960 B2
(45) Date of Patent: *Nov. 16, 2010

(54) ENCAPSULATED ACTIVE MATERIAL CONTAINING NANOSCALED MATERIAL

(75) Inventors: Yabin Lei, Holmdel, NJ (US); Lewis Michael Popplewell, Morganville, NJ (US); Carol Joyce, Toms River, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 428 days.

This patent is subject to a terminal disclaimer.

(21) Appl. No.: 11/611,501

(22) Filed: Dec. 15, 2006

(65) Prior Publication Data

US 2008/0146478 A1    Jun. 19, 2008

(51) Int. Cl.
*C11D 7/60* (2006.01)
(52) U.S. Cl. ..................................... 510/441
(58) Field of Classification Search ............... None
See application file for complete search history.

(56) References Cited

U.S. PATENT DOCUMENTS

| | | |
|---|---|---|
| 2,800,457 A | 7/1957 | Green et al. |
| 3,041,288 A | 6/1962 | Anthony |
| 3,415,758 A | 12/1968 | Powell et al. |
| 3,516,846 A | 6/1970 | Matson |
| 3,516,941 A | 6/1970 | Matson |
| 3,870,542 A | 3/1975 | Ida et al. |
| 3,888,689 A | 6/1975 | Maekawa et al. |
| 4,089,800 A * | 5/1978 | Temple .................. 427/213.31 |
| 4,145,184 A | 3/1979 | Brain et al. |
| 4,318,818 A | 3/1982 | Letton et al. |
| 4,387,090 A | 6/1983 | Bolich, Jr. |
| 4,395,541 A | 7/1983 | Jacquet et al. |
| 4,406,816 A | 9/1983 | Siliwka |
| 4,424,134 A | 1/1984 | Sissin et al. |
| 4,446,042 A | 5/1984 | Leslie |
| 4,515,705 A | 5/1985 | Moeddel |
| 4,520,142 A | 5/1985 | Leinen |
| 4,534,891 A | 8/1985 | Boden et al. |
| 4,537,706 A | 8/1985 | Severson, Jr. |
| 4,537,707 A | 8/1985 | Severson, Jr. |
| 4,550,862 A | 11/1985 | Barker et al. |
| 4,561,998 A | 12/1985 | Wertz et al. |
| 4,597,962 A | 7/1986 | Grollier et al. |
| 4,673,568 A | 6/1987 | Grollier et al. |
| 4,705,681 A | 11/1987 | Maes et al. |
| 4,714,562 A | 12/1987 | Roselle et al. |
| 4,767,547 A | 8/1988 | Straathof et al. |
| 4,968,457 A | 11/1990 | Welch |
| 5,085,857 A | 2/1992 | Reid et al. |
| 5,112,688 A | 5/1992 | Michael |
| 5,126,061 A | 6/1992 | Michael |
| 5,145,842 A | 9/1992 | Driedger et al. |
| 5,169,552 A | 12/1992 | Wise |
| 5,194,639 A | 3/1993 | Connor et al. |
| 5,275,755 A | 1/1994 | Sebag et al. |
| 5,288,417 A | 2/1994 | Baner et al. |
| 5,288,431 A | 2/1994 | Huber et al. |
| 5,324,444 A * | 6/1994 | Berry et al. .................. 512/4 |
| 5,403,499 A | 4/1995 | Kiefer et al. |
| 5,411,671 A | 5/1995 | Baner et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,470,512 A * | 11/1995 | Noji et al. .................. 264/4.1 |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,591,146 A | 1/1997 | Hasse |
| 5,597,936 A | 1/1997 | Perkins et al. |
| 5,618,523 A | 4/1997 | Zysman et al. |
| 5,661,118 A | 8/1997 | Cauwet et al. |
| 5,674,832 A | 10/1997 | Keys |
| 5,679,630 A | 10/1997 | Baeck et al. |

(Continued)

FOREIGN PATENT DOCUMENTS

WO    WO 03/043729    3/2003

(Continued)

OTHER PUBLICATIONS

Devore, David I., and Stephen A. Fischer. "Wet -strength mechanism of polyaminoamide- epichlorohydrin resins". Tappi Journal vol. 76, No. 8 (1993) : pp. 121-128.

(Continued)

*Primary Examiner*—John R Hardee
(74) *Attorney, Agent, or Firm*—Elizabeth M. Quirk; XuFan Tseng; Joseph F. Leightner

(57) ABSTRACT

The present invention is directed to novel capsules containing active material and nanoscaled material and to methods for making capsules with enhanced performance and stability. The capsules are well suited for use in personal care applications, laundry products and perfume and fragrance products.

21 Claims, No Drawings

U.S. PATENT DOCUMENTS

| | | | |
|---|---|---|---|
| 5,703,030 A | 12/1997 | Peakins et al. | |
| 5,703,034 A | 12/1997 | Offshack et al. | |
| 5,705,464 A | 1/1998 | Scheper et al. | |
| 5,731,278 A | 3/1998 | Nair et al. | |
| 5,756,436 A | 5/1998 | Royce et al. | |
| 5,759,990 A | 6/1998 | Wahl et al. | |
| 5,776,443 A | 7/1998 | Vinski et al. | |
| 5,837,661 A | 11/1998 | Evans et al. | |
| 5,849,313 A | 12/1998 | Fast et al. | |
| 5,877,145 A | 3/1999 | Wahl et al. | |
| 5,902,781 A | 5/1999 | Painter | |
| 5,914,307 A | 6/1999 | DeNome et al. | |
| 5,916,862 A | 6/1999 | Morelli et al. | |
| 5,929,022 A | 7/1999 | Velazquez | |
| 5,932,203 A | 8/1999 | Coffundaffer et al. | |
| 5,935,561 A | 8/1999 | Inman et al. | |
| 5,939,373 A | 8/1999 | Haeggberg et al. | |
| 5,962,386 A | 10/1999 | Scheper et al. | |
| 5,968,286 A | 10/1999 | Crudele et al. | |
| 5,968,881 A | 10/1999 | Haeggberg et al. | |
| 5,990,065 A | 11/1999 | Vinson et al. | |
| 6,017,871 A | 1/2000 | Baeck et al. | |
| 6,020,294 A | 2/2000 | Getty et al. | |
| 6,069,122 A | 5/2000 | Vinson et al. | |
| 6,162,423 A | 12/2000 | Sebag et al. | |
| 6,190,678 B1 | 2/2001 | Hasenohrl et al. | |
| 6,200,554 B1 | 3/2001 | Yeoh et al. | |
| 6,261,483 B1 | 7/2001 | Frank et al. | |
| 6,297,203 B1 | 10/2001 | Guskey et al. | |
| 6,329,057 B1 | 12/2001 | Dungworth et al. | |
| 6,335,315 B1 | 1/2002 | Trinh et al. | |
| 6,368,633 B1 * | 4/2002 | Lou et al. | 424/489 |
| 6,544,497 B2 * | 4/2003 | Zhu et al. | 424/45 |
| 6,545,084 B2 | 4/2003 | Brown et al. | |
| 2002/0096795 A1 | 7/2002 | Chandler | |
| 2003/0132538 A1 | 7/2003 | Chandler | |
| 2003/0138557 A1 | 7/2003 | Allison | |
| 2004/0247690 A1 | 12/2004 | Yang | |
| 2005/0079991 A1 * | 4/2005 | Ranade et al. | 510/457 |
| 2005/0101501 A1 * | 5/2005 | Aussant et al. | 510/296 |
| 2005/0130163 A1 | 6/2005 | Smith et al. | |
| 2006/1293396 | 12/2006 | Bringley et al. | |
| 2007/0082829 A1 * | 4/2007 | Smets et al. | 510/101 |
| 2007/0149435 A1 * | 6/2007 | Koenig et al. | 510/384 |
| 2009/1311295 | 12/2009 | Mathriowitz et al. | |

FOREIGN PATENT DOCUMENTS

WO    WO 2008/009216    1/2008

OTHER PUBLICATIONS

Moyer, W.W., and R.A. Stagg. "Wet Strength in Paper and Paperboard." Tappi Monograph Series No. 29. Tappi Press (1965): Ch.3, pp. 33-37.

* cited by examiner

ENCAPSULATED ACTIVE MATERIAL CONTAINING NANOSCALED MATERIAL

FIELD OF THE INVENTION

The present invention is directed to novel capsules containing active material and nanoscaled material and to methods for making capsules with enhanced performance and stability. The capsules are well suited for use in personal care applications, laundry products and perfume and fragrance products.

BACKGROUND OF THE INVENTION

Encapsulation of active material, such as fragrances, is well known in the art. Encapsulation provides advantages to the fragrance product including the protection of the fragrance in the capsule core by a shell until the fragrance is intended to be delivered. In particular, capsules are often designed to deliver their contents at a desired time by the capsule shell being compromised at the desired time.

The capsule shell can be compromised by various factors such as temperature so that the contents are delivered when the capsule begins to melt. Alternatively the capsules can be compromised by physical forces, such as crushing, or other methods that compromise the integrity of the capsule. Additionally, the capsule contents may be delivered via diffusion through the capsule wall during a desired time interval.

It is obviously not desired that the core be released from the shell prematurely. Often, the capsule shell is somewhat permeable to the core contents when stored under certain conditions. This is particularly the case when many capsule types, such as those having aminoplast or cross-linked gelatin walls, are stored in aqueous bases, particularly those containing surfactants. In these cases, although the capsule shell is intact, the fragrance is removed from the core over time in a leaching process. The overall leaching mechanism may be viewed as a diffusion process, with transfer occurring from the capsule core to the aqueous media, followed by transfer to or solubilization into the surfactant micelles or vesicles. With normal surfactant concentrations of between 4 and 30% in consumer products, as compared to fragrance levels of 0.3 to 1%, it is clear that the partitioning favors absorption by the surfactant over time.

In order to enhance the effectiveness of the fragrance material for the user, various technologies such as the encapsulation of the fragrance material in a polymeric protective coating have been employed to enhance the delivery of the fragrance material at the desired time. The polymeric material is used to protect the fragrance material from evaporation, reaction, oxidation or otherwise dissipating prior to use.

While encapsulation of fragrance in a polymeric shell can help prevent fragrance degradation and loss, it is often not sufficient to significantly improve fragrance performance in consumer products. In view of the existing technology, there is an ongoing need to develop fragrance systems which are designed to retain the fragrance with minimal losses until it is needed and then be able to deliver the fragrance at the appropriate time.

The use of nanoscaled material has been recently reported for pharmaceutical application. The main method of encapsulation has been limited to the physical blending of nanoscaled emulsions with active ingredients and the processing afterwards either by freeze, spray or fluidized bed drying process. There are several deficiencies of the process. The active ingredient has generally been limited to solids and the loading of the system is very low. Because of the process involved, the nanostructure of the material is not ensured in the final product. Additionally, a matrix based system will have limited use in applications such as fragrance delivery where robust stability is needed. Polymer systems have been researched and commercialized as fragrance and flavor delivery systems to facilitate application and for better performance, however the delivery system employed is either a polymer matrix or capsule. The use of the nanoscaled material as part of the fragrance core material in fragrance capsules has not been disclosed. The benefits of produced capsules with controlled physical dimensions and consumer benefits of such encapsulated systems have not been discussed before. This may be due to the technical challenges of creating a true nanodispered system for such applications and the difficulties in creating a true core/shell structure involving this type of material.

The use of micro-sized and nanoscaled titanium dioxide and zinc oxide in personal care product have been documented. Both oxides have been incorporated into sunscreen product to protect the skin from harmful UV radiations. The material is often emulsified into person care cream or gel. The use of encapsulated titanium dioxide or zinc oxides in rinse off products has not been disclosed. As a delivery system, these oxides have not been used directly in consumer products such as rinse conditioner because of their hydrophobic properties.

We have now discovered that nanoscaled material can be encapsulated in combination with active material to obtain capsules containing active and nanoscaled material. The fragrance capsules containing nanoscaled material have unique physical and application properties and superior performance can be obtained by such encapsulates. The delivery system can be used in a range of consumer and personal care applications including rinse conditioner, detergent, cleaners, personal care, hair care, sun screen formulation, liquid makeup, and textile.

SUMMARY OF THE INVENTION

The present invention is directed to a microcapsule comprising an active material, a nanoscaled material and an encapsulating polymer.

In another embodiment of the invention a process for preparing a microcapsule product containing nanoscaled material is provided.

The present invention is well suited for use in rinse off products, which are products that are applied to a substrate and then removed in some manner. These and other embodiments of the present invention will become apparent upon referring to the following FIGURE and description of the invention.

DETAILED DESCRIPTION OF THE INVENTION

According to one embodiment of the invention, capsules particles containing nanoscaled material and active materials are disclosed. The nanoscaled material is dispersed in fragrance oil to form a nanodispersion. This dispersion is then used as the core material and encapsulated to produce fragrance capsules containing nanoscaled material. The enclosed material retains the nanoscaled material in the capsule core and capsule wall. Capsules with unique physical and performance properties can be obtained by the use of nanoscaled fragrance core.

According to one embodiment of the invention, nanoscaled material may be selected from, but not limited to, metal or metallic particles, metal alloys, polymer particles, wax particles, inorganic particulates, minerals and clay particles.

The metal particles can be selected from a non-limiting list of main group elements, transition metal and post-transition metal elements including aluminum (Al), silica (Si), Titanium (Ti), chromium (Cr), magenase (Mn), iron (Fe), nickel (Ni), cobalt (Co), copper (Cu), gold (Au), silver (Ag), platinum (Pt) and palladium(Pd). Other suitable metallic parcticles can be selected the perirodic table as long as their physical dimension falls into the prescribed region.

Polymer particle of any chemical composition and nature are suitable for the present invention as long as their physical dimension falls into the prescribed region and a liquid core is generated. The polymer particles can be selected from a non-limiting list of polymers and co-copolymer based on polystyrene, polyvinyl acetate, polylactides, polyglycolides, ethylene maleic anhydride copolymer, polyethylene, polypropylene, polyamide, polyimide, polycarbonate, polyester, polyurethane, polyurea, cellulose and cellulose, and combinations and mixture of such polymers.

The inorganic particulate can be selected from a non-limiting list of: silica, titanium dioxide ($TiO_2$), zinc oxide (ZnO), $Fe_2O_3$, and other metal oxides such as but not limited to NiO, $Al_2O_3$, SnO, $SnO_2$, $CeO_2$, ZnO, CdO, $RuO_2$, FeO, $Fe_2O_3$, CuO, AgO, $Au_2O_3$, $MnO_2$, $WO_2$, $WO_3$ as well as other transition metal oxides.

Examples of nanoscaled material include Aerosil R 812 that has particle size of less than 25 nm according specification from the manufacture, Degussa Corp. Other suitable material from Degussa include, but not limited to, Aerosil R 972, Aerosil R 974, Aerosil R 104, Aerosil R 106, Aerosil R 202, Aerosil R 805, Aerosil R 812, Aerosil R 812 S, Aerosil R 816, Aerosil R 7200, Aerosil R 9200, and Aeroxide $TiO_2$ P25, Aeroxide T 805, Aeroxide LE 1, Aeroxide LE 2, Aeroxide $TiO_2$ NKT 90, Aeroxide Alu C 805, titanium dioxide PF2, Sipernat D110, Sipernat D-380. The hydrophobic materials from Deguassa Corp. such as including Aerosile R812 and R972 are especially preferred.

Nanoscaled materials such as Uvinul $TiO_2$, Z-COTE HP1 manufactured by BASF can also be used as well as and Ti-Pure® titanium dioxide, Ti-Pure® R-700, and Ti-Select™ TS-6200 from Dupont. Additional suitable material includes Zerofree 516, Huberderm 2000, Huberderm 1000 from the J.M. Huber Corporation, Havre De Grace, Md., USA. Silica products such as SYLOID 63, 244, 72, 63FP 244FP, 72FP, SYLOX 15, 2 and Zeolites such as Sylosiv A3, Sylosiv A4 and Sylosiv K300 from Grace Davison can also be used.

The core material can be selected from material with dimensions ranging from a few nanometers to few microns, preferably less than 1000 nm, more preferably with a particle size of less than 500 nm and most preferably with a particle size of less than 100 nm. In addition, hydrophobically modified nanoscaled material is preferred. The core material may be hollow, porous, meso-porous, nano-porous or completed filled. The core material can also be of any regular or irregular shape including sphere, square, needles, fibers, and ellipsoids.

In one embodiment nanoscaled hydrophobic silica such as Aerosil R812, hydrophic titanium dioxide and zinc oxides are enclosed in the core. The rutile form of titanium dioxide is preferred over the anatase form of $TiO_2$.

In another embodiment a combination of nanoscaled material can be used in the capsule. For example, the core composition can consist of mixture of nanoscaled silica and titanium dioxide. The ratio of silica and $TiO_2$ is chosen so that optimal performance can be obtained and can very from about 0.01 to about 10 weight percent (%). The density of the fragrance oil determines how much nanoscaled material will be needed to ensure homogenous distribution of fragrance capsules in a base. The amount of nanoscaled material incorporated into the fragrance capsules is dependent upon both the fragrance ingredients and the product base the capsules are incorporated into. The amount of nanoscaled material incorporated in the core can vary from about 1% to about 50%, preferably less than about 30%, more preferably less than about 20% and most preferably less than about 10%. The optimal amount of nanoscaled material is selected so that the core is still liquid and so that performance of the system can be optimized.

The physical dimension of capsule that can be produced from the invention can be from about 1000 μm to about 50 nm, preferably from about 500 μm to about 1000 nm and most preferably from about 200 μm to about 4 μm.

Without wishing to be bound by any theory it is believed that the nanoscaled material prevents the encapsulated fragrance material from leaching from the capsule. Although the encapsulation material is provided to prevent the loss of fragrance before usage, it is believed that the surfactants found in detergents, fabric conditioners, shampoos and other wash-off products over time leach some of the fragrance from the capsule during storage and before use. The addition of the nanoscaled material to the fragrance-containing capsule material is believed to be incorporated into both the core and the wall of the capsule thus preventing the leaching of the fragrance. The nanoscaled material migrates to the interface of the capsule wall and inures itself in the capsule wall increasing stability, thereby providing additional and longer lasting fragrance to be delivered over time. Also, the inclusion of abrasive nanoscaled material can induce capsule breakage when they are deposited onto the substrates and are perturbed with external forces. It can also promote the self-diffusion of fragrance molecules if the nanostructures can extend into the other region of the capsule. All these factors can lead to more desirable release profiles and superior performance.

In a preferred embodiment the microcapsule product retains greater than 40% of the encapsulated active material after a four week period in consumer products with a tendency to promote leaching of the active material out of the microcapsule product into the base. Such as those that are based on surfactants, alcohols, or volatile silicones can also leach active materials from capsules over time. In a more preferred embodiment the microcapsule product retains greater than 50% of the encapsulated active material after a four week period. In a most preferred embodiment the microcapsule product retains greater than 60% of the encapsulated active material. Retention capabilities may vary dependent on the formulation of the product base, such as the level of surfactant which may range from 1% to 50% as well as the nature of the encapsulated active material and storage temperature.

Leaching of active material, such as fragrance, occurs not only when stored in the consumer products but also when using detergents, fabric softener and other fabric care products during the wash and rinse cycle during washing. The microcapsules of the present invention also exhibit enhanced stability during the wash and rinse cycle.

The term high stability refers to the ability of a microcapsule product to retain active materials in bases that have a tendency to promote leaching of the active material out of the microcapsule product into the base.

As used herein stability of the product is measured at room temperature or above over a period of at least a week. More preferably the capsules of the present invention are allowed to be stored at 37° C. for more than about two weeks and preferably more than about four weeks.

The benefits of fragrance capsule can be demonstrated by perfumery benefits they bring into consumer products. The efficacy of a consumer product containing capsule can be measured by the perfumery intensity before (the pre-rubbing intensity) and after (the post rubbing intensity) any physical force is applied to the substrates. The substrates can include clothing (fabric), hair and skin as well as other fragranced products. As it is common for consumers or fragrance users to expect good and strong "smell" when they are in contact with a perfumed object, it is often beneficial for the products to possesses an higher pre-rubbing intensity in additional to an high overall intensity. This can significantly improve the substantivity of the products and can be quite useful in consumer products including conditioners, shampoo, and body wash where a higher pre-rubbing intensity is often desirable. A higher post-rubbing intensity suggests good fragrance transfer and deposition and is very useful for sustained perfumery benefits in consumer products.

We have surprisingly discovered that the encapsulation of nanoscaled material in fragrance capsules has significantly increased the pre-rubbing intensity of the consumer products containing these capsules while maintaining a high post-rubbing fragrance intensity. The finished product has a more favorable release profile and can delivery the perfumery benefits at all stages of application.

The incorporation of nanoscaled materials into a liquid core also brings additional benefits to the capsule slurry. The high specific density of $SiO_2$ (2.2 g/cm3) and its excellent miscibility with fragrance oils allows one to adjust the density of core material in such way that the fragrance capsules will have a density that is optimally matched with the density of the dispersed phase such as water. As a result, the capsules will distribute homogenously in the slurry for uniform dosing. The Theological property of the slurry is also dramatically improved since there will be no creaming occurring. This can greatly facilitate the application of the product.

Multi-component and multi-functional capsule systems with different physical and performance properties utilizing the unique properties of nanoscaled material can be prepared by the current invention. For example, ultra-violet (UV) absorbing material such as titanium dioxide or zinc oxide can be blended with different type of silica to give capsule that can have good UV protection and excellent consumer benefits.

According to one embodiment of the invention, additional permutations of mixing the different nanoscaled material can easily be generated by those skilled in the art so that the product can be used in personal care skin, hair care and textiles.

According to another embodiment of the invention, the current invention will enable the facile and precise control of the wall thickness of the capsules by adjusting the concentration of the polymer solution. By employing liquid process, capsules with uniform thickness can be prepared easily and the physical property of the capsules can be processed for optimal performance in a wide range of product bases. A wide range of anionic, cationic and neutral polymers can also be used during processing that allow for the systematic modification of the hydrophobic, hydrophilic, and electrostatic property of the capsules so it can be tailed to facilitate the specific application of the encapsulated material.

The active material suitable for use in the present invention can be a wide variety of material in which one would want to deliver in a controlled-release manner onto the surfaces being treated with the present compositions or into the environment surrounding the surfaces. Non-limiting examples of active material include perfumes, flavoring agents, fungicide, brighteners, antistatic agents, wrinkle control agents, fabric softener actives, hard surface cleaning actives, skin and/or hair conditioning agents, malodour counteractants, antimicrobial actives, UV protection agents, insect repellents, animal/vermin repellants, flame retardants, and the like.

In a preferred embodiment, the active material is a fragrance, in which case the microcapsules containing fragrance provide a controlled-release scent onto the surface being treated or into the environment surrounding the surface. In this case, the fragrance can be comprised of a number of fragrance raw materials known in the art, such as essential oils, botanical extracts, synthetic fragrance material and the like.

In general, the active material is contained in the microcapsule at a level of from about 0.1 to about 99 weight percent (%), preferably from about 1% to about 90%, and more preferably from about 5% to about 60%, by weight of the total microcapsule. The weight of the total microcapsule includes the weight of the shell of the microcapsule plus the weight of the material inside the microcapsule.

In another embodiment of the invention a process for preparing a microcapsule product which comprises the steps of admixing a nanoscaled material and a liquid fragrance oil to form a nanodispersion; encapsulating the nanodispersion with a crosslinked network of polymers and curing the polymer encapsulated product at a temperature above 90° C. to provide a microcapsule product.

Previously, it was known in the art to cure capsules at temperatures up to 85° C. and more preferably up to 50° C. The capsules were not cured above these temperatures because there was no perceived advantage. Due to the nature of the polymers used to encapsulate the active materials and the volatile nature of the fragrance components which would be compromised under increased curing temperatures, it would not be expected that increasing the curing temperature would provide capsules with improved retention capabilities. Furthermore, there is also novelty in the engineering process of curing the capsules at temperatures over 90° C., to obtain this, pressure vessels are used during the processing. According to the present invention it is desirable to reach the target cure temperature with a linear heat profile. The high stability of the microcapsules of the present invention is unexpected since it was believed that the aqueous microcapsules would not be stable with increased heat.

Surprisingly, as disclosed in one embodiment of the invention, the crosslinked network of polymers containing active materials cured at high temperatures and for periods of time greater than one hour provide a microcapsule product capable of retaining a much wider range of active materials during storage in consumer product bases that contain surfactants, alcohols, volatile silicones and mixtures thereof than previously possible. For example enhanced retention may be achieved with materials with lower clogp values.

According to one embodiment the retention capabilities of the microcapsule product are improved when the crosslinked network of polymers containing active materials are cured at temperatures above 90° C. In a more preferred embodiment the retention capabilities of microcapsule product are improved when the cure temperature is above 110° C. In a most preferred embodiment the retention capabilities of the microcapsule product are improved when the cure temperature is above 120° C. In a further embodiment the crosslinked network of polymers containing active materials may be cured for periods of time longer up to 1 hour and more preferably longer than two hours.

According to a further embodiment of the invention there is a direct relationship between higher cure temperature and less leaching of active material from the microcapsule.

Furthermore, higher performance of the microcapsules can be achieved by curing at a higher temperature for a longer time.

Encapsulation of active material such as fragrances is known in the art, see for example U.S. Pat. Nos. 2,800,457, 3,870,542, 3,516,941, 3,415,758, 3,041,288, 5,112,688, 6,329,057, and 6,261,483. Another discussion of fragrance encapsulation is found in the Kirk-Othmer Encyclopedia.

The encapsulation process is a very critical step in the current invention. Without encapsulation, the mixture of nanoscaled material and fragrance core has limited direct applications as the materials are highly hydrophobic and incompatible with aqueous solution in which many of the products are formulated. The innovation process in the current invention makes this possible because the unique properties of the nanoscaled material are beneficially utilized.

Preferred encapsulating polymers include those formed from, acrylates, acrylamide, acrylate-co-acrylamide, melamine-formaldehyde or urea-formaldehyde condensates, as well as similar types of aminoplasts. Other wall forming materials include polyurethane, polysiloxanes, polyurea, polyamide, polyimide, polyvinyl alcohol, polyanhydride, polyolefin, polysulfone, polysaccaharide, protein, polylactide (PLA), polyglycolide (PGA), polyorthoester, polyphosphazene, silicone, lipid, modified cellulose, gums, polystyrene, and polyesters or combinations of these materials. Other polymeric materials that are functional are ethylene maleic anyhydride copolymer, styrene maleic anyhydride copolymer, ethylene vinyl acetate copolymer, and lactide glycolide copolymer. Bio-polymers that are derived from alginate, chitosan, collegen, dextran, gelatin, and starch can also be used as the encapsulating materials. Additionally, microcapsules made via the simple or complex coacervation of gelatin are also preferred for use with the coating.

The ratio of wall forming polymer to that of core by weight independent of the slurry composition falls in the range of about 1:100 to about 50:1, more preferable in the range of about 1:50 to about 25:1, even more preferable in the range of about 1:25 to about 10:1 and most preferably of about 1:10 to about 5:1.

A representative process used for aminoplast encapsulation is disclosed in U.S. Pat. No. 3,516,941 though it is recognized that many variations with regard to material and process steps are possible. A representative process used for gelatin encapsulation is disclosed in U.S. Pat. No. 2,800,457 though it is recognized that many variations with regard to material and process steps are possible. Both of these processes are discussed in the context of fragrance encapsulation for use in consumer products in U.S. Pat. Nos. 4,145,184 and 5,112,688 respectively.

Well known material such as solvents, surfactants, emulsifiers, and the like can be used in addition to the polymers described throughout the invention to encapsulate the active material such as fragrance without departing from the scope of the present invention. It is understood that the term encapsulated is meant to mean that the active material is substantially covered in its entirety. Encapsulation can provide pore vacancies or interstitial openings depending on the encapsulation techniques employed. More preferably the entire active material portion of the present invention is encapsulated.

Fragrance capsules known in the art consists of a core of various ratios of fragrance and solvent material, a wall or shell comprising a three-dimensional cross-linked network of an aminoplast resin, more specifically a substituted or un-substituted acrylic acid polymer or co-polymer cross-linked with a urea-formaldehyde pre-condensate or a melamine-formaldehyde pre-condensate.

Microcapsule formation using mechanisms similar to the foregoing mechanism, using (i) melamine-formaldehyde or urea-formaldehyde pre-condensates and (ii) polymers containing substituted vinyl monomeric units having proton-donating functional group moieties (e.g. sulfonic acid groups or carboxylic acid anhydride groups) bonded thereto is disclosed in U.S. Pat. No. 4,406,816 (2-acrylamido-2-methylpropane sulfonic acid groups), UK published Patent Application GB 2,062,570 A (styrene sulfonic acid groups) and UK published Patent Application GB 2,006,709 A (carboxylic acid anhydride groups).

The cross-linkable acrylic acid polymer or co-polymer microcapsule shell wall precursor has a plurality of carboxylic acid moieties, to wit:

The cross-linkable acrylic acid polymer or co-polymer microcapsule shell wall precursor has a plurality of carboxylic acid moieties, to wit:

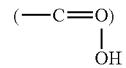

an is preferably one or a blend of the following:
(i) an acrylic acid polymer;
(ii) a methacrylic acid polymer;
(iii) an acrylic acid-methacrylic acid co-polymer;
(iv) an acrylamide-acrylic acid co-polymer;
(v) a methacrylamide-acrylic acid co-polymer;
(vi) an acrylamide-methacrylic acid co-polymer;
(vii) a methacrylamide-methacrylic acid co-polymer;
(viii) a $C_1$-$C_4$ alkyl acrylate-acrylic acid co-polymer;
(ix) a $C_1$-$C_4$ alkyl acrylate-methacrylic acid co-polymer;
(x) a $C_1$-$C_4$ alkyl methacrylate-acrylic acid co-polymer;
(xi) a $C_1$-$C_4$ alkyl methacrylate-methacrylic acid co-polymer;
(xii) a $C_1$-$C_4$ alkyl acrylate-acrylic acid-acrylamide co-polymer;
(xiii) a $C_1$-$C_4$ alkyl acrylate-methacrylic acid-acrylamide co-polymer;
(xiv) a $C_1$-$C_4$ alkyl methacrylate-acrylic acid-acrylamide co-polymer;
(xv) a $C_1$-$C_4$ alkyl methacrylate-methacrylic acid-acrylamide co-polymer;
(xvi) a $C_1$-$C_4$ alkyl acrylate-acrylic acid-methacrylamide co-polymer;
(xvii) a $C_1$-$C_4$ alkyl acrylate-methacrylic acid-methacrylamide co-polymer;
(xviii) a $C_1$-$C_4$ alkyl methacrylate-acrylic acid-methacrylamide co-polymer; and
(xix) a $C_1$-$C_4$ alkyl methacrylate-methacrylic acid-methacrylamide co-polymer;
and more preferably, an acrylic acid-acrylamide copolymer.

When substituted or un-substituted acrylic acid co-polymers are employed in the practice of our invention, in the case of using a co-polymer having two different monomeric units, e.g. acrylamide monomeric units and acrylic acid monomeric units, the mole ratio of the first monomeric unit to the second monomeric unit is in the range of from about 1:9 to about 9:1, preferably from about 3:7 to about 7:3. In the case of using a co-polymer having three different monomeric units, e.g. ethyl methacrylate, acrylic acid and acrylamide, the mole ratio of the first monomeric unit to the second monomeric unit to the third monomeric unit is in the range of 1:1:8 to about 8:8:1, preferably from about 3:3:7 to about 7:7:3.

The molecular weight range of the substituted or un-substituted acrylic acid polymers or co-polymers useful in the practice of our invention is from about 5,000 to about 1,000,000, preferably from about 10,000 to about 100,000. The substituted or un-substituted acrylic acid polymers or co-polymers useful in the practice of our invention may be branched, linear, star-shaped, dendritic-shaped or may be a block polymer or copolymer, or blends of any of the aforementioned polymers or copolymers.

Such substituted or un-substituted acrylic acid polymers or co-polymers may be prepared according to any processes known to those skilled in the art, for example, U.S. Pat. No. 6,545,084.

The urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing our invention, the resulting material has a molecular weight in the range of from 156 to 3000. The resulting material may be used 'as-is' as a cross-linking agent for the aforementioned substituted or un-substituted acrylic acid polymer or copolymer or it may be further reacted with a C1-C6 alkanol, e.g. methanol, ethanol, 2-propanol, 3-propanol, 1-butanol, 1-pentanol or 1-hexanol, thereby forming a partial ether where the mole ratio of melamine or urea:formalhyde:alkanol is in the range of 1:(0.1-6):(0.1-6). The resulting ether moiety-containing product may by used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 3,516,846, U.S. Pat. No. 6,261,483, and Lee et al. J. Microencapsulation, 2002, Vol. 19, No. 5, pp 559-569, "Microencapsulation of fragrant oil via in situ polymerization: effects of pH and melamine-formaldehyde molar ratio". Examples of urea-formaldehyde pre-condensates useful in the practice of our invention are URAC 180 and URAC 186, trademarks of Cytec Technology Corp. of Wilmington, Del. 19801, U.S.A. Examples of melamine-formaldehyde pre-condensates useful in the practice of our invention are CYMEL U-60, CYMEL U-64 and CYMEL U-65, trademarks of Cytec Technology Corp. of Wilmington, Del. 19801, U.S.A. In the practice of our invention it is preferable to use as the precondensate for cross-linking the substituted or un-substituted acrylic acid polymer or co-polymer. The melamine-formaldehyde pre-condensate having the structure:

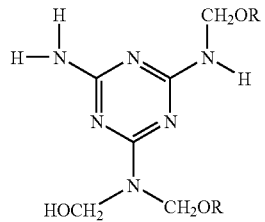

wherein each of the R groups are the same or different and each represents hydrogen or C1-C6 lower alkyl, e.g. methyl, ethyl, 1-propyl, 2-propyl, 1-butyl, 2-butyl, 2-methyl-1-propyl, 1-pentyl, 1-hexyl and/or 3-methyl-1-pentyl.

In practicing our invention, the range of mole ratios of urea-formaldehyde precondensate or melamine-formaldehyde pre-condensate: substituted or un-substituted acrylic acid polymer or co-polymer is in the range of from about 9:1 to about 1:9, preferably from about 5:1 to about 1:5 and most preferably from about 2:1 to about 1:2.

In another embodiment of the invention, microcapsules with polymer(s) comprising primary and/or secondary amine reactive groups or mixtures thereof and crosslinkers as disclosed in commonly assigned U.S. patent application Ser. No. 11/123,898.

The amine polymers can possess primary and/or secondary amine functionalities and can be of either natural or synthetic origin. Amine containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the Lupamin series of polyvinyl formamides (available from BASF). The molecular weights of these materials can range from 10,000 to 1,000,000.

The polymers containing primary and/or secondary amines can be used with any of the following comonomers in any combination:

1. Vinyl and acrylic monomers with:
    a. alkyl, aryl and silyl substituents;
    b. OH, COOH, SH, aldehyde, trimonium, sulfonate, NH2, NHR substiuents;
    c. vinyl pyridine, vinyl pyridine-N-oxide, vinyl pyrrolidon
2. Cationic monomers such as dialkyl dimethylammonium chloride, vinyl imidazolinium halides, methylated vinyl pyridine, cationic acrylamides and guanidine-based monomers
3. N-vinyl formamide and any mixtures thereof. The ratio amine monomer/total monomer ranges from 0.01-0.99, more preferred from 0.1-0.9.

The following represents a general formula for the amine-containing polymer material:

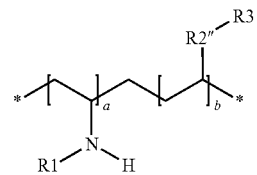

wherein R is a saturated or unsaturated alkane, dialkylsiloxy, dialkyloxy, aryl, alkylated aryl, and that may further contain a cyano, OH, COOH, NH2, NHR, sulfonate, sulphate, —NH2, quaternized amines, thiols, aldehyde, alkoxy, pyrrolidone, pyridine, imidazol, imidazolinium halide, guanidine, phosphate, monosaccharide, oligo or polysaccharide.

R1 is H, CH3, (C=O)H, alkylene, alkylene with unsaturated C—C bonds, CH2-CROH, (C=O)—NH—R, (C=O)—(CH2)n-OH, (C=O)—R, (CH2)n-E, —(CH2-CH(C=O))n-XR, —(CH2)n-COOH, —(CH2)n-NH2, —CH2)n-(C=O)NH2, E is an electrophilic group; wherein a and b are integers or average numbers (real numbers) from about 100-25,000.

R2 can be nonexistent or the functional group selected from the group consisting of —COO—, —(C=O)—, —O—, —S—, —NH—(C=O)—, —NR1-, dialkylsiloxy, dialkyloxy, phenylene, naphthalene, alkyleneoxy. R3 can be the same or selected from the same group as R1.

Additional copolymers with amine monomers are provided having the structure:

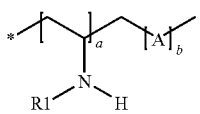

R1 is H, CH3, (C=O)H, alkylene, alkylene with unsaturated C—C bonds, CH2-CROH, (C=O)—NH—R, (C=O)—(CH2)n-OH, (C=O)—R, (CH2)n-E, —(CH2-CH(C=O))n-XR, —(CH2)n-COOH, —(CH2)n-NH2, —CH2)n-(C=O)NH2, E is an electrophilic group; wherein a and b are integers or average numbers (real numbers) from about 100-25,000; wherein R is a saturated or unsaturated alkane, dialkylsiloxy, dialkyloxy, aryl, alkylated aryl, and that may further contain a cyano, OH, COOH, NH2, NHR, sulfonate, sulphate, —NH2, quaternized amines, thiols, aldehyde, alkoxy, pyrrolidone, pyridine, imidazol, imidazolinium halide, guanidine, phosphate, monosaccharide, oligo or polysaccharide.

The comonomer, represented by A, can contain an amine monomer and a cyclic monomer wherein A can be selected from the group consisting of aminals, hydrolyzed or non-hydrolyzed maleic anhydride, vinyl pyrrolidine, vinyl pyridine, vinyl pyridine-N-oxide, methylated vinyl pyridine, vinyl naphthalene, vinyl naphthalene-sulfonate and mixtures thereof.

When A is an aminal the following general structure can represent the aminal:

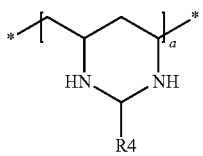

wherein R4 is selected from the group consisting of H, CH3, (C=O)H, alkylene, alkylene with unsaturated C—C bonds, CH2-CROH, (C=O)—NH—R, (C=O)—(CH2)n-OH, (C=O)—R, (CH2)n-E, —(CH2-CH(C=O))n-XR, —(CH2)n-COOH, —(CH2)n-NH2, —CH2)n-(C=O)NH2, E is an electrophilic group; wherein R is a saturated or unsaturated alkane, dialkylsiloxy, dialkyloxy, aryl, alkylated aryl, and that may further contain a cyano, OH, COOH, NH2, NHR, sulfonate, sulphate, —NH2, quaternized amines, thiols, aldehyde, alkoxy, pyrrolidone, pyridine, imidazol, imidazolinium halide, guanidine, phosphate, monosaccharide, oligo or polysaccharide.

In addition instead of amine-containing polymers it is possible to utilize amine-generating polymers that can generate primary and secondary amines during the microcapsule formation process as disclosed in commonly assigned U.S. patent application Ser. No. 11/123,898.

The crosslinkers can be selected from the group consisting of aminoplasts, aldehydes such as formaldehyde and acetaldehyde, dialdehydes such as glutaraldehyde, epoxy, active oxygen such as ozone and OH radicals, poly-substituted carboxylic acids and derivatives such as acid chlorides, anyhydrides, isocyanates, diketones, halide-substituted, sulfonyl chloride-based organics, inorganic crosslinkers such as Ca2+, organics capable of forming azo, azoxy and hydrazo bonds, lactones and lactams, thionyl chloride, phosgene, tannin/tannic acid, polyphenols and mixtures thereof. Furthermore, processes such as free radical and radiation crosslinking can be used according to the present invention. Examples of free radical initiators are benzoyl peroxide, sodium persulfate, azoisobutylnitrile (AIBN) and mixtures thereof.

With respect to the crosslinker, wall properties are influenced by two factors: the degree of crosslinking and the hydrophobic or hydrophilic nature of the crosslinker. The quantity and reactivity of the crosslinker determine the degree of crosslinking. The degree of crosslinking influences the microcapsule wall permeability by forming physical barriers towards diffusion. Walls made from crosslinkers possessing low-reactive groups will have smaller degrees of crosslinking than walls made from high-reactive crosslinkers. If a high degree of crosslinking is desired from a low-reactive crosslinker, more is added. If a low degree of crosslinking is desired from a high-reactive crosslinker then less is added. The nature and quantity of the crosslinker can also influence the hydrophobicity/hydrophilicity of the wall. Some crosslinkers are more hydrophobic than others and these can be used to impart hydrophobic qualities to the wall, with the degree of hydrophobicity directly proportional to the quantity of crosslinker used.

The degree of crosslinking and degree of hydrophobicity can result from a single crosslinker or a combination of crosslinkers. A crosslinker that is highly reactive and hydrophobic can be used to create microcapsule walls with a high degree of crosslinking and a hydrophobic nature. Single crosslinkers that possess both these qualities are limited and thus crosslinker blends can be employed to exploit these combinations. Crosslinkers possessing high reactivities but low hydrophobicities can be used in combination with a low reactive, high hydrophobicity crosslinker to yield walls with high degrees of crosslinking and high hydrophobicity. Suitable crosslinkers are disclosed in commonly assigned U.S. patent application Ser. No. 11/123,898.

(A) Copolymers containing primary and/or secondary amine. When amine-containing polymers are employed in the practice of the invention, in the case of using a co-polymer having two different monomeric units, e.g. Lupamin 9030 (copolymer of vinyl amine and vinyl formamide), the mole ratio of the first monomeric unit to the second monomeric unit is in the range of from about 0.1:0.9 to about 0.9:0.1, preferably from about 1:9 to about 9:1. In the case of using a co-polymer having three different monomeric units, e.g. a copolymer of vinyl amine, vinyl formamide and acrylic acid, the mole ratio of the reactive monomer (i.e. vinyl amine+acrylic acid) in the total polymer ranging from about 0.1 to about 0.9, more preferably from about 1 to about 9.

(B) Branched amine containing polymers such as ethylene imines (Lupasol series of BASF) and ethoxylated ethylene imines.

(C) Mixtures of amine containing polymers and other polymers that contain other reactive groups such as COOH, OH, and SH.

The molecular weight range of the substituted or un-substituted amine-containing polymers or co-polymers and mixtures thereof, useful in the practice of our invention is from about 1,000 to about 1,000,000, preferably from about 10,000 to about 500,000. The substituted or un-substituted amine-containing polymers or co-polymers useful in the practice of our invention may be branched, linear, star-shaped, graft, ladder, comb/brush, dendritic-shaped or may be a block polymer or copolymer, or blends of any of the aforementioned polymers or copolymers. Alternatively, these polymers may also possess thermotropic and/or lyotropic liquid crystalline properties.

As disclosed in commonly assigned U.S. application Ser. No. 10/720,524, particles comprised of fragrance and a variety of polymeric and non-polymeric matrixing material is also suitable for use. These may be composed of polymers such as polyethylene, fats, waxes, or a variety of other suitable material. Essentially any capsule, particle, or dispersed droplet may be used that is reasonably stable in the application and release of fragrance at an appropriate time once deposited.

Particle and microcapsule diameter can vary from about 10 nanometers to about 1000 microns, preferably from about 50 nanometers to about 100 microns and most preferably from about 1 to about 15 microns. The microcapsule distribution can be narrow, broad, or multi-modal. Each modal of the multi-modal distributions may be composed of different types of microcapsule chemistries.

Once the fragrance material is encapsulated a cationically charged water-soluble polymer may be applied to the fragrance encapsulated polymer. This water-soluble polymer can also be an amphoteric polymer with a ratio of cationic and anionic functionalities resulting in a net total charge of zero and positive, i.e., cationic. Those skilled in the art would appreciate that the charge of these polymers can be adjusted by changing the pH, depending on the product in which this technology is to be used. Any suitable method for coating the cationically charged material onto the encapsulated fragrance material can be used. The nature of suitable cationically charged polymers for assisted microcapsule delivery to interfaces depends on the compatibility with the microcapsule wall chemistry since there has to be some association to the microcapsule wall. This association can be through physical interactions, such as hydrogen bonding, ionic interactions, hydrophobic interactions, electron transfer interactions or, alternatively, the polymer coating could be chemically (covalently) grafted to the microcapsule or particle surface. Chemical modification of the microcapsule or particle surface is another way to optimize anchoring of the polymer coating to microcapsule or particle surface. Furthermore, the microcapsule and the polymer need to want to go to the desired interface and, therefore, need to be compatible with the chemistry (polarity, for instance) of that interface. Therefore, depending on which microcapsule chemistry and interface (e.g., cotton, polyester, hair, skin, wool) is used the cationic polymer can be selected from one or more polymers with an overall zero (amphoteric: mixture of cationic and anionic functional groups) or net positive charge, based on the following polymer backbones: polysaccharides, polypeptides, polycarbonates, polyesters, polyolefinic (vinyl, acrylic, acrylamide, poly diene), polyester, polyether, polyurethane, polyoxazoline, polyamine, silicone, polyphosphazine, olyaromatic, poly heterocyclic, or polyionene, with molecular weight (MW) ranging from about 1,000 to about 1000,000,000, preferably from about 5,000 to about 10,000,000. As used herein molecular weight is provided as weight average molecular weight. Optionally, these cationic polymers can be used in combination with nonionic and anionic polymers and surfactants, possibly through coacervate formation.

A more detailed list of cationic polymers that can be used to is provided below:

Polysaccharides include but are not limited to guar, alginates, starch, xanthan, chitosan, cellulose, dextrans, arabic gum, carrageenan, hyaluronates. These polysaccharides can be employed with:

(a) cationic modification and alkoxy-cationic modifications, such as cationic hydroxyethyl, cationic hydroxy propyl. For example, cationic reagents of choice are 3-chloro-2-hydroxypropyl trimethylammonium chloride or its epoxy version. Another example is graft-copolymers of polyDADMAC on cellulose like in Celquat L-200 (Polyquaternium-4), Polyquaternium-10 and Polyquaternium-24, commercially available from National Starch, Bridgewater, N.J.;

(b) aldehyde, carboxyl, succinate, acetate, alkyl, amide, sulfonate, ethoxy, propoxy, butoxy, and combinations of these functionalities. Any combination of Amylose and Mylopectin and overall molecular weight of the polysaccharide; and (c) any hydrophobic modification (compared to the polarity of the polysaccharide backbone).

The above modifications described in (a), (b) and (c) can be in any ratio and the degree of functionalization up to complete substitution of all functionalizable groups, and as long as the theoretical net charge of the polymer is zero (mixture of cationic and anionic functional groups) or preferably positive. Furthermore, up to 5 different types of functional groups may be attached to the polysaccharides. Also, polymer graft chains may be differently modified than the backbone. The counterions can be any halide ion or organic counter ion. As disclosed in U.S. Pat. Nos. 6,297,203 and 6,200,554.

Another source of cationic polymers contain protonatable amine groups so that the overall net charge is zero (amphoteric: mixture of cationic and anionic functional groups) or positive. The pH during use will determine the overall net charge of the polymer. Examples are silk protein, zein, gelatin, keratin, collagen and any polypeptide, such as polylysine.

Further cationic polymers include poly vinyl polymers, with up to 5 different types of monomers, having the monomer generic formula —C(R2)(R1)-CR2R3-. Any co-monomer from the types listed in this specification may also be used. The overall polymer will have a net theoretical positive charge or equal to zero (mixture of cationic and anionic functional groups). Where R1 is any alkanes from C1-C25 or H; the number of double bonds ranges from 0-5. Furthermore, R1 can be an alkoxylated fatty alcohol with any alkoxy carbon-length, number of alkoxy groups and C1-C25 alkyl chain length. R1 can also be a liquid crystalline moiety that can render the polymer thermotropic liquid crystalline properties, or the alkanes selected can result in side-chain melting. In the above formula R2 is H or CH3; and R3 is —Cl, —NH2 (i.e., poly vinyl amine or its copolymers with N-vinyl formamide. These are sold under the name Lupamin 9095 by BASF Corporation), —NHR1, —NR1R2, —NR1R2 R6 (where R6=R1, R2, or —CH2-COOH or its salt), —NH—C(O)—H, —C(O)—NH2 (amide), —C(O)—N(R2)(R2')(R2"), —OH, styrene sulfonate, pyridine, pyridine-N-oxide, quaternized pyridine, imidazolinium halide, imidazolium halide, imidazol, piperidine, pyrrolidone, alkyl-substituted pyrrolidone, caprolactam or pyridine, phenyl-R4 or naphthalene-R5 where R4 and R5 are R1, R2, R3, sulfonic acid or its alkali salt —COOH, —COO— alkali salt, ethoxy sulphate or any other organic counter ion. Any mixture or these R3 groups may be used. Further suitable cationic polymers containing hydroxy alkyl vinyl amine units, as disclosed in U.S. Pat. No. 6,057,404.

Another class of material is polyacrylates, with up to 5 different types of monomers, having the monomer generic formula:

—CH(R1)-C(R2)(CO—R3-R4)-. Any co-monomer from the types listed in this specification may also be used. The overall polymer will have a net theoretical positive charge or equal to zero (mixture of cationic and anionic functional groups). In the above formula R1 is any alkane from C1-C25 or H with number of double bonds from 0-5, aromatic moieties, polysiloxane, or mixtures thereof. Furthermore, R1 can be an alkoxylated fatty alcohol with any alkoxy carbon-length, number of alkoxy groups and C1-C25 alkyl chain length. R1 can also be a liquid crystalline moiety that can render the polymer thermotropic liquid crystalline properties, or the alkanes selected can result in side-chain melting. R2 is H or CH3; R3 is alkyl alcohol C1-25 or an alkylene oxide with any number of double bonds, or R3 may be absent such that the C=O bond is (via the C-atom) directly connected to R4. R4 can be: —NH2, NHR1, —NR1R2, —NR1R2 R6 (where R6=R1, R2, or —CH2-COOH or its salt), —NH—C(O)—, sulfo betaine, betaine, polyethylene oxide, poly(ethyleneoxide/propylene oxide/butylene oxide) grafts with any end group, H, OH, styrene sulfonate, pyridine, quaternized pyridine, alkyl-substituted pyrrolidone or pyridine, pyridine-N-oxide, imidazolinium halide, imidazolium halide, imidazol, piperidine, —OR1, —OH, —COOH alkali salt, sulfonate, ethoxy sulphate, pyrrolidone, caprolactam, phenyl-R4 or naphthalene-R5 where R4 and R5 are R1, R2, R3, sulfonic acid or its alkali salt or organic counter ion. Any mixture or these R3 groups may be used. Also, glyoxylated cationic polyacrylamides can be used. Typical polymers of choice are those containing the cationic monomer dimethylaminoethyl methacrylate (DMAEMA) or methacrylamidopropyl trimethyl ammonium chloride (MAPTAC). DMAEMA can be found in Gafquat and Gaffix VC-713 polymers from ISP. MAPTAC can be found in BASF's Luviquat PQ11 PN and ISP's Gafquat HS100.

Another group of polymers that can be used are those that contain cationic groups in the main chain or backbone. Included in this group are:

(1) polyalkylene imines such as polyethylene imine, commercially available as Lupasol from BASF. Any molecular weight and any degree of crosslinking of this polymer can be used in the present invention;

(2) ionenes having the general formula set forth as —[N(+)R1R2-A1-N(R5)-X—N(R6)-A2-N(+)R3R4-A3]n-2Z—, as disclosed in U.S. Pat. Nos. 4,395,541 and 4,597,962;

(3) adipic acid/dimethyl amino hydroxypropyl diethylene triamine copolymers, such as Cartaretin F-4 and F-23, commercially available from Sandoz;

(4) polymers of the general formula —[N(CH3)2-(CH2)x-NH—(CO)—NH—(CH2)y-N(CH3)2)-(CH2)z-O—(CH2)p]n-, with x, y, z, p=1-12, and n according to the molecular weight requirements. Examples are Polyquaternium 2 (Mirapol A-15), Polyquaternium-17 (Mirapol AD-1), and Polyquaternium-18 (Mirapol AZ-1).

Other polymers include cationic polysiloxanes and cationic polysiloxanes with carbon-based grafts with a net theoretical positive charge or equal to zero (mixture of cationic and anionic functional groups). This includes cationic end-group functionalized silicones (i.e. Polyquaternium-80). Silicones with general structure: —[—Si(R1)(R2)-O-]x-[Si(R3)(R2)-O-]y- where R1 is any alkane from C1-C25 or H with number of double bonds from 0-5, aromatic moieties, polysiloxane grafts, or mixtures thereof. R1 can also be a liquid crystalline moiety that can render the polymer thermotropic liquid crystalline properties, or the alkanes selected can result in side-chain melting. R2 can be H or CH3 and R3 can be —R1-R4, where R4 can be —NH2, —NHR1, —NR1R2, —NR1R2R6 (where R6=R1, R2, or —CH2-COOH or its salt), —NH—C(O)—, —COOH, —COO— alkali salt, any C1-25 alcohol, —C(O)—NH2 (amide), —C(O)—N(R2)(R2')(R2"), sulfo betaine, betaine, polyethylene oxide, poly (ethyleneoxide/propylene oxide/butylene oxide) grafts with any end group, H, —OH, styrene sulfonate, pyridine, quaternized pyridine, alkyl-substituted pyrrolidone or pyridine, pyridine-N-oxide, imidazolinium halide, imidazolium halide, imidazol, piperidine, pyrrolidone, caprolactam, —COOH, —COO— alkali salt, sulfonate, ethoxy sulphate phenyl-R5 or naphthalene-R6 where R5 and R6 are R1, R2, R3, sulfonic acid or its alkali salt or organic counter ion. R3 can also be —(CH2)x-O—CH2-CH(OH)—CH2-N(CH3)2-CH2-COOH and its salts. Any mixture of these R3 groups can be selected. X and y can be varied as long as the theoretical net charge of the polymer is zero (amphoteric) or positive. In addition, polysiloxanes containing up to 5 different types of monomeric units may be used. Examples of suitable polysiloxanes are found in U.S. Pat. Nos. 4,395,541 4,597,962 and 6,200,554. Another group of polymers that can be used to improve microcapsule/particle deposition are phospholipids that are modified with cationic polysiloxanes. Examples of these polymers are found in U.S. Pat. No. 5,849,313, WO Patent Application 9518096A1 and European Patent EP0737183B1.

Furthermore, copolymers of silicones and polysaccharides and proteins can be used (commercially available as CRODASONE brand products).

Another class of polymers include polyethylene oxide-co-propyleneoxide-co-butylene oxide polymers of any ethylene oxide/propylene oxide/butylene oxide ratio with cationic groups resulting in a net theoretical positive charge or equal to zero (amphoteric). The general structure is:

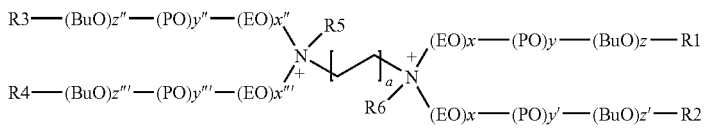

where R1,2,3,4 is —NH2, —N(R)3-X+, R with R being H or any alkyl group. R5, 6 is —CH3 or H. The value for 'a' can range from 1-100. Counter ions can be any halide ion or organic counter ion. X,Y, may be any integer, any distribution with an average and a standard deviation and all 12 can be different. Examples of such polymers are the commercially available TETRONIC brand polymers.

Suitable polyheterocyclic (the different molecules appearing in the backbone) polymers include the piperazine-alkylene main chain copolymers disclosed in Ind. Eng. Chem. Fundam., (1986), 25, pp. 120-125, by Isamu Kashiki and Akira Suzuki.

Also suitable for use in the present invention are copolymers containing monomers with a cationic charge in the primary polymer chain, up to 5 different types of monomers may be used. Any co-monomer from the types listed in this specification may also be used. Examples of such polymers are poly diallyl dimethyl ammonium halides (PolyDADMAC) copolymers of DADMAC with vinyl pyrrolidone, acrylamides, imidazoles, imidazolinium halides, etc. These polymers are disclosed in Henkel EP0327927A2 and PCT Patent Application 01/62376A1. Also suitable are Polyquaternium-6 (Merquat 100), Polyquaternium-7 (Merquats S, 550, and 2200), Polyquaternium-22 (Merquats 280 and 295) and Polyquaternium-39 (Merquat Plus 3330), available from Ondeo Nalco.

Polymers containing non-nitrogen cationic monomers of the general type —CH2-C(R1)(R2-R3-R4)- can be used with:

R1 being a —H or C1-C20 hydrocarbon. R2 is a disubstituted benzene ring or an ester, ether, or amide linkage. R3 is a C1-C20 hydrocarbon, preferably C1-C10, more preferably C1-C4. R4 can be a trialkyl phosphonium, dialkyl sulfonium, or a benzopyrilium group, each with a halide counter ion. Alkyl groups for R4 are C1-C20 hydrocarbon, most preferably methyl and t-butyl. These monomers can be copolymerized with up to 5 different types of monomers. Any co-monomer from the types listed in this specification may also be used.

Substantivity of these polymers may be further improved through formulation with cationic, amphoteric and nonionic surfactants and emulsifiers, or by coacervate formation between surfactants and polymers or between different polymers. Combinations of polymeric systems (including those mentioned previously) may be used for this purpose as well as those disclosed in EP1995/000400185.

Furthermore, polymerization of the monomers listed above into a block, graft or star (with various arms) polymers can often increase the substantivity toward various surfaces. The monomers in the various blocks, graft and arms can be selected from the various polymer classes listed in this specification and the sources below:

Encyclopedia of Polymers and Thickeners for Cosmetics, Robert Lochhead and William From, in Cosmetics & Toiletries, Vol. 108, May 1993, pp. 95-138;

Modified Starches: Properties & Uses, O. B. Wurzburg, CRC Press, 1986. Specifically, Chapters 3, 8, and 10;

U.S. Pat. Nos. 6,190,678 and 6,200,554; and

PCT Patent Application WO 01/62376A1 assigned to Henkel.

Polymers, or mixtures of the following polymers:

(a) Polymers comprising reaction products between polyamines and (chloromethyl) oxirane or (bromomethyl) oxirane. Polyamines being 2(R1)N—[—R2-N(R1)-]n-R2-N (R1)2, 2HN—R1-NH2, 2HN—R2-N(R1)2 and 1H-Imidazole. Also, the polyamine can be melamine. R1 in the polyamine being H or methyl. R2 being alkylene groups of C1-C20 or phenylene groups. Examples of such polymers are known under the CAS numbers 67953-56-4 and 68797-57-9. The ratio of (chloromethyl) oxirane to polyamine in the cationic polymer ranges from 0.05-0.95.

(b) Polymers comprising reaction products of alkanedioic acids, polyamines and (chloromethyl) oxirane or (bromomethyl) oxirane. Alkane groups in alkanedioic acids C0-C20. Polyamine structures are as mentioned in (a). Additional reagents for the polymer are dimethyl amine, aziridine and polyalkylene oxide (of any molecular weight but, at least, di-hydroxy terminated; alkylene group being C1-20, preferably C2-4). The polyalkylene oxide polymers that can also be used are the Tetronics series. Examples of polymers mentioned here are known under the CAS numbers 68583-79-9 (additional reagent being dimethyl amine), 96387-48-3 (additional reagent being urea), and 167678-45-7 (additional reagents being polyethylene oxide and aziridine). These reagents can be used in any ratio.

(c) Polyamido Amine and Polyaminoamide-epichlorohydrin resins, as described by David Devore and Stephen Fisher in Tappi Journal, vol. 76, No. 8, pp. 121-128 (1993). Also referenced herein is "Polyamide-polyamine-epichlorohydrin resins" by W. W. Moyer and R. A. Stagg in Wet-Strength in Paper and Paperboard, Tappi Monograph Series No. 29, Tappi Press (1965), Ch. 3, 33-37.

The preferred cationically charged material comprises reaction products of polyamines and (chloromethyl) oxirane. In particular, reaction products of 1H-imidazole and (chloromethyl) oxirane, known under CAS number 68797-57-9. Also preferred are polymers comprising reaction products of 1,6-hexanediamine,N-(6-aminohexyl) and (chloromethyl) oxirane, known under CAS number 67953-56-4. The preferred weight ratio of the imidazole polymer and the hexanediamine, amino hexyl polymer is from about 5:95 to about 95:5 weight percent and preferably from about 25:75 to about 75:25.

The encapsulated systems can be prepared by several processes. In one process, the nanoscaled material is pre-blended with the fragrance oil under slight shear to form homogenous dispersion. This mixture can then be used as core. The coating polymer is pre-formed with suitable monomers. The core material is then sheared into an aqueous solution of the coating polymer at the desired concentration. The polymerization reaction is allowed to proceed further under constant agitation at elevated temperature. The polymerization reaction is stopped after the reaction or encapsulation is complete. Encapsulation of the core material can be monitored by optical microscope. The collected slurry can be used in any direct application.

In another process, the core composition is directly blended into the polymer precursor solution under shearing. The polymerization reaction is allowed to proceed further under constant agitation at elevated temperature. The polymerization reaction is stopped after the reaction is complete. The progress of reaction and encapsulation of the core material can be monitored by optical microscope. The collected slurry can be used in any direct application.

According to the present invention, the encapsulated fragrance is well suited for a variety of applications, including wash-off products. Wash-off products are understood to be those products that are applied for a given period of time and then are removed. These products are common in areas such as laundry products, and include detergents, fabric conditioners, and the like; as well as personal care products which include shampoos, conditioner, hair colors and dyes, hair rinses, body washes, soaps and the like.

Microcapsules containing an active material, preferably perfume, suitable for use in the present compositions are described in detail in, e.g., U.S. Pat. Nos. 3,888,689; 4,520, 142; 5,126,061; and 5,591,146.

The fragrances suitable for use in this invention include without limitation, any combination of fragrance, essential oil, plant extract or mixture thereof that is compatible with, and capable of being encapsulated by a polymer.

Many types of fragrances can be employed in the present invention, the only limitation being the compatibility and ability to be encapsulated by the polymer being employed, and compatibility with the encapsulation process used. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal scents such as rosemary, thyme, and sage; and woodland scents derived from pine, spruce and other forest smells. Fragrances may also be derived from various oils, such as essential oils, or from plant material such as peppermint, spearmint and the like. Other familiar and popular smells can also be employed such as baby powder, popcorn, pizza, cotton candy and the like in the present invention.

A list of suitable fragrances is provided in U.S. Pat. Nos. 4,534,891, 5,112,688 and 5,145,842. Another source of suitable fragrances is found in Perfumes Cosmetics and Soaps, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like. Those with skill in the art appreciate that fragrance formulations are frequently complex mixtures of many fragrance ingredients. A perfumer commonly has several thousand fragrance chemicals to work from. Those with skill in the art appreciate that the present invention may contain a single ingredient, but it is much more likely that the present invention will comprise at least eight or more fragrance chemicals, more likely to contain twelve or more and often twenty or more fragrance chemicals. The present invention also contemplates the use of complex fragrance formulations containing fifty or more fragrance chemicals, seventy five or more or even a hundred or more fragrance chemicals in a fragrance formulation.

The level of fragrance in the microcapsule product varies from about 0.1 to about 95 weight percent (%), preferably from about 1 to about 80 weight % and most preferably from about 5 to about 60 weight %. In addition to the fragrance, other material can be used in conjunction with the fragrance and are understood to be included.

As used herein olfactory effective amount is understood to mean the amount of compound in perfume compositions the individual component will contribute to its particular olfactory characteristics, but the olfactory effect of the fragrance composition will be the sum of the effects of each of the fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

As noted above, the fragrance may also be combined with a variety of solvents which serve to increase the compatibility of the various material, increase the overall hydrophobicity of the blend, influence the vapor pressure of the material, or serve to structure the blend. Solvents performing these functions are well known in the art and include mineral oils, triglyceride oils, silicone oils, fats, waxes, fatty alcohols, diisodecyl adipate and diethyl phthalate among others.

A common feature of many encapsulation processes is that they require the fragrance material to be encapsulated to be dispersed in aqueous solutions of polymers, pre-condensates, surfactants, and the like prior to formation of the capsule walls. Therefore, material having low solubility in water, such as highly hydrophobic material are preferred, as they will tend to remain in the dispersed perfume phase and partition only slightly into the aqueous solution. Fragrance material with Clog P values greater than 1, preferably greater than 3, and most preferably greater than 5 will thus result in microcapsules that contain cores most similar to the original composition, and will have less possibility of reacting with material that form the capsule shell.

One object of the present invention is to deposit capsules containing fragrance cores on desired substrates such as cloth, hair, and skin during washing and rinsing processes. Further, it is desired that, once deposited, the capsules release the encapsulated fragrance either by diffusion through the capsule wall, via small cracks or imperfections in the capsule wall caused by drying, physical, or mechanical means, or by large-scale rupture of the capsule wall. In each of these cases, the volatility of the encapsulated perfume material is critical to both the speed and duration of release, which in turn control consumer perception. Thus, fragrance chemicals which have higher volatility as evidenced by normal boiling points of less than 250° C., preferably less than about 225° C. are preferred in cases where quick release and impact of fragrance is desired. Conversely, fragrance chemicals that have lower volatility (boiling points greater than 225° C.) are preferred when a longer duration of aroma is desired. Of course, fragrance chemicals having varying volatility may be combined in any proportions to achieve the desired speed and duration of perception.

The present active material compositions may further comprise one or more malodour counteractant at a level preferably less than about 70 weight %, more preferably less than about 50 weight % of the composition. The malodour counteractant composition serves to reduce or remove malodor from the surfaces or objects being treated with the present compositions. The malodour counteractant composition is preferably selected from uncomplexed cyclodextrin, odor blockers, reactive aldehydes, flavanoids, zeolites, activated carbon, and mixtures thereof. Compositions herein that comprise odor control agents can be used in methods to reduce or remove malodor from surfaces treated with the compositions.

Specific examples of malodour counteractant components useful in aminoplast microencapsulate used in the composition and process of our invention are as follows:

Malodour Counteractant Component Group I:
1-cyclohexylethan-1-yl butyrate;
1-cyclohexylethan-1-yl acetate;
1-cyclohexylethan-1-ol;
1-(4'-methylethyl)cyclohexylethan-1-yl propionate; and
2'-hydroxy-1'-ethyl(2-phenoxy)acetate each of which compound is marketed under the trademark VEILEX by International Flavors & Fragrances Inc., New York, N.Y., U.S.A. Malodour Counteractant Component Group II, as disclosed in U.S. Pat. No. 6,379,658:
  β-naphthyl methyl ether;
  β-naphthyl ketone;
  benzyl acetone;
mixture of hexahydro-4,7-methanoinden-5-yl propionate and hexahydro-4,7-methanoinden-6-yl propionate;
4-(2,6,6-trimethyl-2-cyclohexen-1-yl)-3-methyl-3-buten-2-one;
3,7-dimethyl-2,6-nonadien-1-nitrile;
dodecahydro-3a,6,6,9a-tetramethylnaphtho(2,1-b)furan;
ethylene glycol cyclic ester of n-dodecanedioic acid;
1-cyclohexadecen-6-one;
1-cycloheptadecen-10-one; and
corn mint oil.

In addition to the fragrance material in the present invention contemplates the incorporation of solvent material into the microcapsule product. The solvent material is a hydrophobic material that are miscible in the fragrance material used in the present invention. The solvent material serves to increase the compatibility of various active material, increase the overall hydrophobicity of the blend, influence the vapor pressure of active material, or serve to structure the blend. Suitable solvents are those having reasonable affinity for the fragrance chemicals and a ClogP greater than 2.5, preferably greater than 3.5 and most preferably greater that 5.5. Suitable solvent material include, but are not limited to triglyceride oil, mono and diglycerides, mineral oil, silicone oil, diethyl phthalate, polyalpha olefins, castor oil and isopropyl myristate. In a preferred embodiment the solvent material are combined with fragrance material that have ClogP values as set forth above. It should be noted that selecting a solvent and fragrance with high affinity for each other will result in the most pronounced improvement in stability. Appropriate solvents may be selected from the following non-limiting list:

Mono-, di- and tri-esters, and mixtures thereof, of fatty acids and glycerine. The fatty acid chain can range from C4-C26. Also, the fatty acid chain can have any level of unsaturation. For instance capric/caprylic triglyceride known as Neobee M5 (Stepan Corporation). Other suitable examples are the Capmul series by Abitec Corporation. For instance, Capmul MCM.

Isopropyl myristate

Fatty acid esters of polyglycerol oligomers:

R2CO—[OCH2-CH(OCOR1)-CH2O-]n, where R1 and R2 can be H or C4-26 aliphatic chains, or mixtures thereof, and n ranges between 2-50, preferably 2-30.

Nonionic fatty alcohol alkoxylates like the Neodol and Dobanol surfactants by Shell Corporation or the BioSoft surfactants by Stepan or Utensil by BASF. The alkoxy group being ethoxy, propoxy, butoxy or mixtures thereof. In addition, these surfactants can be end-capped with methyl groups in order to increase their hydrophobicity.

Di- and tri-fatty acid chain containing nonionic, anionic and cationic surfactants, and mixtures thereof.

Fatty acid esters of polyethylene glycol, polypropylene glycol, and polybutylene glycol, or mixtures thereof.

Polyalphaolefins such as the ExxonMobil PureSym™ PAO line

Esters such as the ExxonMobil PureSyn™ Esters

Mineral oil

Silicone oils such polydimethyl siloxane and polydimethylcyclosiloxane

Diethyl phthalate

Di-isodecyl adipate

While no solvent is needed in the core, in one embodiment the level of solvent in the core of the microcapsule product weight percent should be greater than about 20 weight %, preferably greater than about 50 weight % and most preferably less than about 50 weight %. In addition to the solvent it is preferred that higher ClogP fragrance materials are employed. It is preferred that greater than about 25 weight %, preferably greater than 50 weight % and more preferably greater than about 80 weight % of the fragrance chemicals have ClogP values of greater than about 2.0, preferably greater than about 3.0 and most preferably greater than about 3.5. Those with skill in the art will appreciate that many formulations can be created employing various solvents and fragrance chemicals. The use of high ClogP fragrance chemicals will require a lower level of hydrophobic solvent than fragrance chemicals with lower ClogP to achieve similar stability. As those with skill in the art will appreciate, in a highly preferred embodiment high ClogP fragrance chemicals and hydrophobic solvents comprise greater than about 80 weight %, preferably more than about 90 weight % and most preferably greater than 99 weight % of the fragrance composition.

A common feature of many encapsulation processes is that they require the fragrance material to be encapsulated to be dispersed in aqueous solutions of polymers, pre-condensates, surfactants, and the like prior to formation of the microcapsule walls.

In order to provide the highest fragrance impact from the fragrance encapsulated microcapsules deposited on the various substrates referenced above, it is preferred that material with a high odor-activity be used. Material with high odor-activity can be detected by sensory receptors at low concentrations in air, thus providing high fragrance perception from low levels of deposited microcapsules. This property must be balanced with the volatility as described above. Some of the principles mentioned above are disclosed in U.S. Pat. No. 5,112,688.

As described herein, the present invention is well suited for use in a variety of well-known consumer products such as laundry detergent and fabric softeners, liquid dish detergents, automatic dish detergents, as well as hair shampoos and conditioners, deodorants and anti-perspirants. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. All of the above mentioned U.S. Patents.

According to another embodiment the retention capabilities of the microcapsule product are improved when the crosslinked network of polymers containing active material are cured at temperatures above 90° C. In a more preferred embodiment the retention capabilities of microcapsule product are improved when the cure temperature is above 110° C. In a most preferred embodiment the retention capabilities of the microcapsule product are improved when the cure temperature is above 130° C. In a further embodiment the crosslinked network of polymers containing active material may be cured for periods of time longer than 1 hour and more preferably longer than two hours.

All U.S. Patents and patent applications cited herein are incorporated by reference as if set forth herein in their entirety.

The following examples are provided as specific embodiments of the present invention. These and additional modifications and improvements of the present invention may also be apparent to those with ordinary skill in the art. The particular combinations of elements described and illustrated herein are intended only to represent only a certain embodiment of the present invention and are not intended to serve as limitations of alternative articles within the spirit and scope of the invention. All materials are reported in weight percent unless noted otherwise. As used herein all percentages are understood to be weight percent.

Example I

This example illustrates the application of present innovation in producing fragrance encapsulate with nanoscaled silica.

In this example, 6 grams (herein referred to as g) of Aerosil R812 (Degussa Corporation) was blended with 99 g of NEOBEE M5 oil (Stephan Company, Northfield, Ill.) and Spring Blush fragrance (International Flavors & Fragrances Inc., IFF, Union Beach, N.J., USA) in a 16 oz jar. The mixture was slightly sheared to generate a homogenously dispersed and nanostructured fragrance core to be encapsulated later. The silica had a particle size range from 15 to 40 nm according to manufacturing specification. In a separate reaction vessel, 34 g of a copolymer of acryl amide and acrylic acid was first dispersed in 300 ml of water together with 18 g of a methylated melamine-formaldehyde resin. These two components were allowed to react under acidic conditions for the desired amount of time at room temperature. The nanostructured core material was then added to polymer solution. The system was subject to high shear homogenization to promote the formation of capsules by the pre-formed polymer. Curing of the polymeric layer around the fragrance encapsulate was achieved by increasing the temperature from 50 to 150° C. and maintaining the temperature for desired amount of time. The slurry was collected for future use.

It was demonstrated that the production of fragrance capsules with nanostructured core is easily accomplished using the present invention.

Example II

This example illustrates the use of the present invention in producing fragrance encapsulate containing another nanostructured material.

In this experiment, 12 g of Aeroxide LE 1 (Degussa Corporation) was mixed with 92 g of NEOBEE M5 oil (Stephan Company, Northfield, Ill.) and 105 gram of the fragrance Apple/Brilliance (80/20 mixture) in a 16 Oz jar under stirring to form the nanostructured core to be encapsulated. This mixture of fragrance oil, solvent and nanoscaled silica was encapsulated similarly according to the process in Example I.

Example III

This example illustrates the versatility of the current invention in producing fragrance capsules.

In this experiment, 105 g of NEOBEE M5 oil [Stephan Company, Northfield, Ill.] and 105 gram of the fragrance Spring Blush commercially available from IFF were mixed in a 16 Oz jar under stirring to form the fragrance core to be encapsulated. This mixture of fragrance oil and solvent was encapsulated similarly according to the process in Example I.

Example IV

This example demonstrates the use of a nanoscaled core in controlling the capsule size of fragrance capsules.

The particle size of the capsule was measured using a Malvern Mastersize 2000e (Malvern Instruments Ltd., Worcestershire, United Kingdom) A 1% dilution of the capsule slurry was prepared and sonicated on a sonicator (Branson) for 30 minutes before measurement was taken. The measured capsule size is tabulated in the table below.

| Capsule system | Measured Capsule size |
|---|---|
| Spring Blush capsule without nanoscaled silica in the core (Aerosil R812) | 5.2 µm |
| Spring blush capsule with 3% of nanoscaled silica in the core (Aerosil R812) | 7.5 µm |

It is quite clear that the inclusion of nanoscaled silica in the core has increased the capsule size by almost 50%. This discovery can be used to engineering capsules with desirable physical dimensions with optimal performance.

Example V

This example illustrates the unique perfumery benefit of fragrance capsules containing nanoscaled materials.

This was established by blending the capsule slurry into a commercially available rinse conditioner (RC) solution, Snuggle (Unilever) and conducting laundry experiment using the Snuggle solution containing the encapsulated fragrance at 0.5% neat fragrance equivalent. 30 g of the RC solution was used to conduct the laundry experiments using U.S. washing machine that typically utilizes 60 liters of water. Terry towels were used for the washing experiments and were machined dried per experimental protocol. The perfumery benefit was evaluated by panel of 16 judges. The fragrance intensity was assigned a value from 0 to 30 according the Labeled Magnitude Scale (LMS) with 0 being no sensation and 30 being strong. The results are tabulated in Table 2 below.

TABLE 2

Tabulation of Sensory Test Results

| Samples | Pre-rubbing intensity ($I_{pre}$) | Post-rubbing intensity ($I_{post}$) |
|---|---|---|
| Blank | 2.6 | 3.1 |
| Neat Fragrance | 4.6 | 4.0 |
| Spring Blush capsule without nanoscaled silica in the core | 6.8 | 11.5 |
| Spring Blush capsule with nanostructured silica in the core (Aerosil R812) | 12.4 | 12.5 |

It is quite apparent that the fragrance capsule containing nanoscaled silica has significantly higher pre-rubbing and post-rubbing intensity than neat fragrance. The perfumery intensity has increased by almost two hundred percent in the pre-rubbing stage and over two hundred percent in the post-rubbing stage. The fragrance capsule with the nanascaled core has significantly higher pre-rubbing intensity than the capsules prepared without the nanoscaled materials. It is also evident that the pre-rubbing intensity of the capsule is almost equal to the post-rubbing intensity. The results clearly demonstrates that the fragrance encapsulate prepared nanoscaled material are able to retain the fragrance effectively and is capable of delivering the full consumer benefits of the fragrance products in both the pre- and post-rubbing stages.

Example VI

This example presents the application and perfumery benefits of fragrance encapsulate containing nanoscaled material in a model hair conditioner product.

Fragrance capsule were prepared with a commercial fragrance Brillance available from IFF and nanoscaled Aerosil R812. The capsules were blended into a model hair conditioner base. Hair washing experiments were conducted using Mannequin heads following well established and industrially accepted protocol. Four products were evaluated and they are: Neat Brilliance fragrance, a market product (MP), a Brillance capsule without nanoscaled silica (capsule minus nanosilica) and Brilliance capsules with nanoscaled silica (capsules+nanosilica). The sensory benefits of the samples were evaluated by a panel of 10 judges. The perfumery intensity was assigned a value from 0 to 10 with 10 being extremely strong and 0 being no sensation. The results are tabulated in table three below.

TABLE 3

Tabulation of Sensory Test Results

| Samples | Pre-rubbing intensity ($I_{pre}$) | Post-rubbing intensity ($I_{post}$) |
| --- | --- | --- |
| Neat Brilliance fragrance | 1.00 | 1.8 |
| market product | 1.88 | 2.50 |
| Brilliance capsule minus nanosilica in core | 2.0 | 5.66 |
| Brilliance capsules + nanosilica in core | 3.44 | 6.31 |

The results demonstrates that the fragrance capsules containing nanoscaled silica has significant higher perfumery intensity than the market product and higher overall intensity than an encapsulated product that does not contain any silica in the core in both the pre-rubbing and post-rubbing stage. The pre-rubbing intensity in the capsule containing the nanoscaled core is almost twice as intense as the market products. The post-rubbing intensity of the capsule containing the nanoscaled core is more than double of that of market product. Compared with the market product, the pre-rubbing intensity was improved. The fragrance release profile is very similar to that of the neat fragrance, but with much stronger intensity. This clearly established that the capsules contain nanoscaled silica can delivery optimal perfumery benefits at all stages of application.

Example VII

This example illustrates the ability of the nanoscaled capsules to retain encapsulated materials in an application base.

The study was conducted in a model hair conditioner base. The typical base is a mixture of water (75%), quaternary surfactant (2%), fatty alcohol (Cetyl and Stearyl Alcohol, 6%), conditioning surfactant/agent (stearamidopropyl dimethylamine, 2%), dimethicone (6%), and other minor ingredients.

Fragrance capsules were prepared with Fruity Pomegranate commercially available from IFF. The capsule core contained 105 g fragrance oil, 12.0 g Aerosil R-812 and 93 g of Neobee oil. The mixture was encapsulated as described in examples I. A control samples was prepared without the inclusion of Aerosile R812 which was replaced with Neobee. The fragrance capsule was blended into the hair conditioner base at 0.6% neat fragrance equivalent. The sample was aged at 37° C. for four weeks. The amount of fragrance leached out in the base was analyzed by direct injection of the base after the capsule was removed from the aged base by a proprietary process. The amount of leached out fragrance was found to be 61% for the control sample, and only 5.3% for the capsule with the nanostructured core. This suggests that over 94% of fragrance oil was retained in the capsules core after 4 weeks at 37° C., a significant improvement in capsule stability.

The example clearly demonstrates the robustness of nanoscaled capsules and its ability to retain the core material over an extended period of time.

Example VIII

This example illustrates the application of the nanoscaled capsules in shampoo application. Because shampoo consists of highly concentrated anionic surfactant solution, the retention of fragrance or other hair care ingredient is very lower in general. However, this problem can be circumvented using the nanoscaled capsule delivery system.

The nanostructure capsule core was prepared by blending 105 g of Fruity Pomegranate commercially available from IFF, 6 g of Aerosil R812 (Degussa) and 99 g of Neobee oil (Stepan). This liquid and nanostructures core was encapsulated according example I. The capsule was then dispersed in a model shampoo base at 1.2% neat equivalent. The base contained approximately 9 to 15% anionic surfactant (SLES, sodium laureath sulfate) and other auxiliary component. The products were then evaluated using standard and industry-acceptable protocol using Mannequin head. Sensory benefits of the samples were evaluated by a panel of 12 judges. The perfumery intensity was assigned a value from 0 to 10 with 10 being extremely strong and 0 being no sensation. The result was contrasted with a leading market product in table 4.

TABLE 4

Performance of nanoscaled capsule in shampoo

| Samples | Pre-rubbing intensity ($I_{pre}$) | Post-rubbing intensity ($I_{post}$) |
| --- | --- | --- |
| Fragranced market product | 1.00 | 1.39 |
| Capsule with nanoscaled core | 2.79 | 7.14 |

The results indicated that the capsule with nanoscaled generates much higher fragrance intensity than the market product in both the pre-rubbing and post-rubbing stage. The perfumery intensity increase near two fold in the pre-rubbing stage and more than four fold in the post-rubbing stage. It is quite apparent that the nanoscaled capsule system can delivery the fragrance effects very efficiently to convey superior consumer benefits in the finished products.

We claim:

1. A microcapsule comprising
an active material, a nanoscaled material selected from the group consisting of silica, titanium oxide, zinc oxide, hematite and mixtures thereof and an encapsulating polymer wherein the encapsulation polymer is mixture of an acrylate polymer, an acrylate acrylamide copolymer and a melamine-formaldehyde polymer.

2. The microcapsule of claim 1 wherein the nanoscaled material is silica.

3. The microcapsule of claim 2 wherein the silica has a particle size range of from about 15 to about 40 nm.

4. The microcapsule of claim 2 wherein the nanoscaled material is less than about 30%.

5. The microcapsule of claim 2 wherein the nanoscaled material is less than about 20%.

6. The microcapsule of claim 2 wherein the nanoscaled material is less than about 10%.

7. The microcapsule of claim 1 wherein the active material is a fragrance and wherein the microcapsule retains greater than 40% of the fragrance after a four week period in a surfactant containing consumer products.

8. The microcapsule of claim 1 wherein the active material is a fragrance and wherein the microcapsule retains greater than 50% of the fragrance after a four week period in a surfactant containing consumer products.

9. The microcapsule claim 1 wherein the nanoscaled material is less than about 50%.

10. The microcapsule of claim 1 which is further coated with a polymer material.

11. The microcapsule of claim 10 wherein the polymer coating is cationically charged.

12. The microcapsule of claim 11 wherein the polymer coating is selected from the group consisting of polysaccharides, cationically modified starch, cationically modified guar, polysiloxanes, poly diallyl dimethyl ammonium halides, copolymers of poly diallyl dimethyl ammonium chloride and vinyl pyrrolidone, acrylamides, imidazoles, imidazolinium halides, imidazolium halides, poly vinyl amine, copolymers of poly vinyl amine and N-vinyl formamide to the surface of the polymer encapsulated fragrance to form a cationically coated polymer encapsulated material.

13. The microcapsule of claim 1 wherein the active material is selected from the group consisting of fragrances, flavoring agents, fungicide, brighteners, antistatic agents, wrinkle control agents, fabric softener actives, hard surface cleaning actives, skin and/or hair conditioning agents, antimicrobial actives, UV protection agents, insect repellants, animal/vermin repellants, flame retardants, and mixtures thereof.

14. The microcapsule of claim 13 wherein said active material is a liquid fragrance.

15. The microcapsule of claim 14 wherein said composition further comprises a malodour counteractant composition.

16. The microcapsule of claim 15 wherein said malodour counteractant composition is selected from the group consisting of uncomplexed cyclodextrin; odor blockers; reactive aldehydes; flavanoids; zeolites; activated carbon; and mixtures thereof.

17. A microcapsule comprising an active material, a nanoscaled material selected from the group consisting of silica, titanium oxide, zinc oxide, hematite and mixtures thereof and an encapsulating op wherein the encapsulating polymer is a crosslinked network of polymers comprising a melamine-formaldehyde:acrylamide acrylic acid copolymer wherein the mole ratio is in the range of from about 9:1 to about 1:9.

18. The microcapsule of claim 17 wherein the mole ratio of melamineformaldehyde:acrylamide-acrylic acid copolymer is in the range of from about 5:1 to about 1:5.

19. The microcapsule of claim 17 wherein the mole ratio of melamineformaldehyde:acrylamide-acrylic acid copolymer is in the range of from about 2:1 to about 1:2.

20. A consumer product selected from the group consisting of detergents, fabric softeners, body washes, soaps, shampoos and hair rinses, anti-perspirants, deodorants, skin creams and hard surface cleaners comprising the microcapsule of claim 1.

21. The consumer product of claim 20 which is a shampoo.

* * * * *